United States Patent [19]

Heimerl et al.

[11] Patent Number: 5,080,275

[45] Date of Patent: Jan. 14, 1992

[54] SURGICAL INSTRUMENT FOR IMPLANTING WOUND STAPLES

[75] Inventors: Albert Heimerl; Holger Kartheus; Hans Pietsch, all of Hamburg; Bernd Voss, Norderstedt, all of Fed. Rep. of Germany

[73] Assignee: Beiersdorf AG, Hamburg, Fed. Rep. of Germany

[21] Appl. No.: 594,296

[22] Filed: Oct. 9, 1990

[30] Foreign Application Priority Data

Oct. 18, 1989 [DE] Fed. Rep. of Germany ....... 3934698

[51] Int. Cl.⁵ .......................................... A61B 17/068
[52] U.S. Cl. .................................... 227/176; 227/19; 227/116; 227/134
[58] Field of Search ................. 227/177, 176, 175, 89, 227/88, 85, 19, 129, 134, 114, 115, 116; 606/143

[56] References Cited

U.S. PATENT DOCUMENTS

| | | | |
|---|---|---|---|
| 4,375,866 | 3/1983 | Giersch et al. | 227/19 |
| 4,411,378 | 10/1983 | Warman | 606/143 X |
| 4,523,707 | 6/1985 | Blake, III. et al. | 227/19 |
| 4,747,531 | 5/1988 | Brinkerhoff et al. | 227/19 |

*Primary Examiner*—Frank T. Yost
*Assistant Examiner*—C. Dexter
*Attorney, Agent, or Firm*—Dvorak and Traub

[57] ABSTRACT

There is disclosed a surgical instrument for implanting in bodily tissue, wound staples each comprising two legs and a crown connecting the legs. The staples are moved in succession out of a magazine onto an anvil, to be deformed thereon by means of a driver. The driver is lowered from a position of rest towards the staple on the anvil, and is further moved to close the staple on the anvil by bending the staple theraround, and to insert the legs of the staple into the bodily tissue. For problem-free and symmmetrical deformation of the staple, a hold-down device is lowered onto the anvil and upon deformation of the staple thereon presses the crown of the staple onto the anvil and so prevents the staple from moving laterally during its deformation.

12 Claims, 5 Drawing Sheets

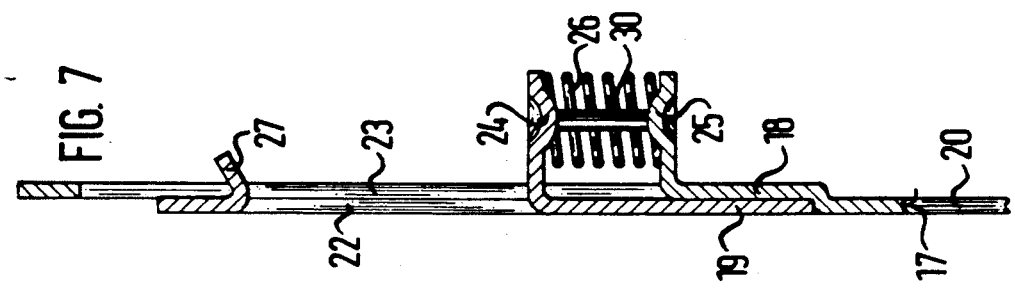
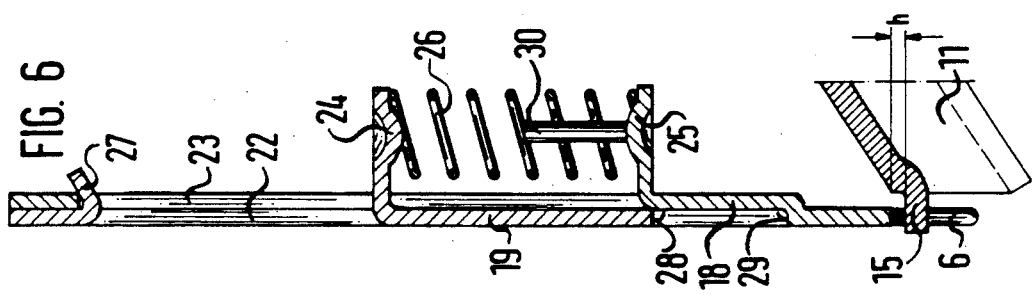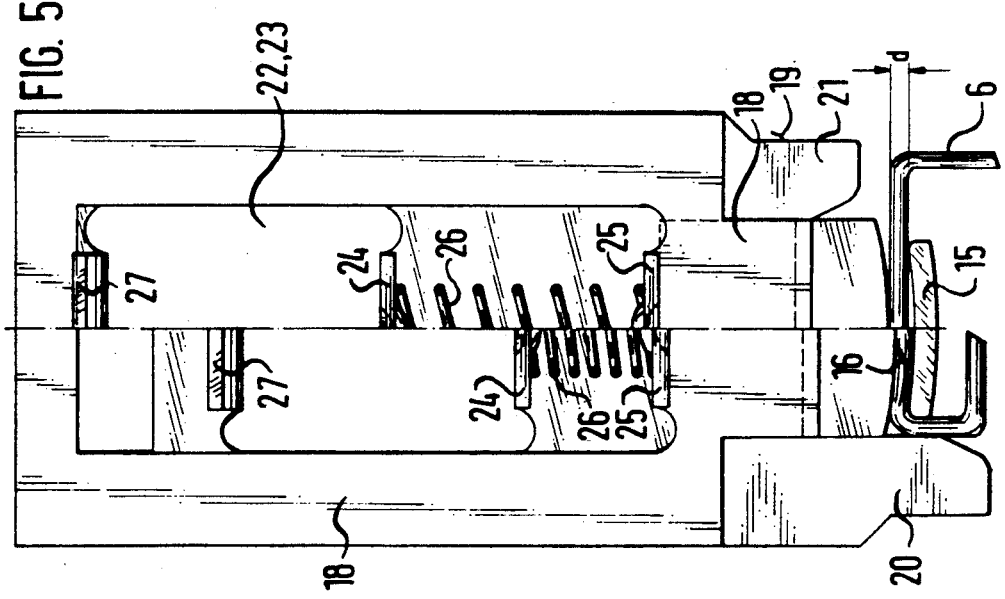

SURGICAL INSTRUMENT FOR IMPLANTING WOUND STAPLES

FIELD OF THE INVENTION

This invention relates to a surgical instrument for implanting, in bodily tissue, wound staples comprising two legs and a crown connecting the legs. The staples are movable in succession out of a magazine onto an anvil to be deformed thereon by a driver. The driver is lowered from a position of rest towards a staple on the anvil and is further displaced, in order to close the staple by bending it about the anvil and to insert the legs of the staple into the tissue.

BACKGROUND OF THE INVENTION

Such wound stapling instruments which are disclosed in EP-A-040 683, EP-A-142 225, EP-A-284 345, EP-A-244 854, U.S. Pat. No. A-1,945,377 and U.S. Pat. No. A-3,873,016, are used in particular for the closure of skin wounds in operations, and are, to an increasing extent, being used instead of the traditional method of stitching wounds.

The use of wound staples does, however, have certain disadvantages in clinical practice. For a scar to heal well, the healing of the wound should begin at the lowermost layer of the skin. The surgeon performing the stapling operation accordingly stands the edges of the wound slightly upwards, before their being stapled, and then secures such so-called "everting" of the wound edges with a staple seam. Where the implantation of the wound staples is poorly carried out, the everting position may not be maintained, resulting in stepped scars which are disadvantageous, both cosmetically and also with regard to the stability of the scar.

This disadvantage may be attributed on the one hand to the shape of the staple being unfavourable, but on the other hand principally to malfunctioning of the wound stapling instrument. It has accordingly been found that the staples are frequently deformed asymmetrically, although they are stored in the staple magazine in precise symmetrical alignment, the dies for deforming the staple, namely on the anvil and the driver, having no detectable asymmetry.

One reason why such asymmetrical deformation of the staple may occur is because during the deformation or closure of the staple, the lower edge region of the staple, lying on the anvil, is displaced with respect to its center. Another reason is that, the arching of the staple which automatically occurs in the region of its crown draws staple material inwards, because the driver presses onto the staple by way of two legs which are directed downwardly onto the staple on both sides of the center of the staple, whereby the crown of the staple is raised from the anvil thereby producing said arching.

For the above reasons, tractive forces acting on the staple are produced at the two contact points between the staple and the anvil. These tractive forces, which are oppositely directed, firstly occur uniformly to the left and to the right, but only until the tractive force exceeds the static friction force at one or other contact point. The staple will then start to slide on one side in the respective contact zone and will continue to slide, because the coefficient of sliding friction, is always less than the coefficient of static friction. The staple will, therefore, always be drawn more towards one side and will not be implanted symmetrically, especially when said slipping of the staple on the anvil is additionally adversely affected by an unfavourable introduction of force by the driver in the same direction. Also, if it is asymmetrically deformed, the staple may jam in the region of the deformation tooling so that the staple can not readily be released.

The material of the staple is usually steel wire. When it is deformed or implanted, a staple of such material is predominantly plastically deformed, although it is always also elastically deformed so that when the staple is released from the dies it reopens slightly and spreads apart. Such spring-back effect has the disadvantage that wound edge adaptation cannot be controlled.

It is proposed according to EP-A-284 345 to compensate for the spring-back effect in such a way that the staple, when being implanted, is also elastically deformed and prestressed against its actual closing direction, so that on release of the implanted staple, such prestressing acts in the closing direction of the staple and thus against the unavoidable spring-back effect. In order to achieve this, a concave depression may be provided in the anvil, and a convex pressure cross-piece, formed complementarily with the depression, provided on the driver. As the driver is lowered, the cross-piece presses the crown of the staple into the depression. The cross-piece is provided on the driver above its two lateral legs which press the legs of the staple into the tissue by correspondingly bending the staple. Because of this construction, when the driver is lowered, only the legs of the driver act initially on the staple and deform it, whilst the pressure cross-piece can only come into action thereafter, or at the earliest shortly before the end of the actual deformation of the staple.

Such an expedient cannot, therefore, prevent the crown of staple from arching with the disadvantages mentioned above, the arching of the staple only being eliminated when said cross-piece arrives at the crown of the staple and presses the crown into the depression. Since the staple has already substantially reached its planned deformation, staple material is drawn over the lateral edges of the anvil in the direction of the center of the depression, so that the staple, by reason of static frictions of different extents occurring at the points of contact of the staple with the anvil, deforms asymmetrically and is clamped between the dies. It is most doubtful that the crown of the staple can be sufficiently elastically prestressed since the staple has already been substantially deformed and firmly fixed between the dies.

The arching of the staple can be limited by means of a stop arranged above the anvil and rigidly connected therewith as disclosed in EP-A-142 225. The crown, which shifts upwards during the deformation of the staple, is inhibited from further arching by means of the stop. However, the staple, or in fact its crown, must be introduced from the side with sufficient play into the space between the anvil and the stop, so that lateral displacement, and thus asymmetrical deformation, of the staple on the anvil can not effectively be prevented, because the stop can not secure the staple crown on the anvil.

SUMMARY OF THE INVENTION

The invention is intended to provide a wound stapling instrument in which completely symmetrical deformation and implantation of the staples is ensured, and in which the elastic spring-back effect of the staple is compensated for, to the greatest possible extent.

According to the invention a hold-down device is arranged to be lowered onto the anvil, to press, upon deformation of the staple on the anvil, the crown of the staple in the direction of the anvil. The crown of the staple is thereby always held under pressure on the anvil, so that the crown of the staple cannot arch on deformation of the staple and cannot be displaced laterally on the anvil.

The driver may be moved together with the hold-down device from the above-mentioned position of rest into an intermediate position, in which only the hold-down device initially rests against the crown of the staple, whilst the driver, under the tension of a spring mechanism acting between the driver and the hold-down device, is further displaced alone in order to deform the staple, the hold-down device being then stationary.

In order to compensate for the elastic spring-back effect and the spreading apart of the staple on release from the dies, that is to say the driver and the anvil, the anvil is formed with a concave depression and the working end of the hold-down device which end is aligned with the depression, is of convex form, such that the staple undergoes elastic deformation in the region of the crown thereof by the hold-down device, such deformation being opposed to the direction of closing of the staple.

Since upon actuation of the instrument, first the hold-down device and then only the driver comes to rest against the staple, said elastic deformation of the staple crown can be effected by its being pressed into the depression by means of the hold-down device, before the staple is deformed by means of the driver, which is then displaced further, to implant the staple. Staple material cannot, therefore, be drawn over the lateral edges of the anvil towards the center of the depression and the staple cannot be deformed asymmetrically, especially since the hold-down device secures the elastically deformed crown portion in the depression against arching and lateral displacement.

The above described chronologically staggered striking of the hold-down device and driver against the staple is, therefore, preferred, although at least approximately identically good results may be achieved if the hold-down device and the driver, are arranged to strike the staple at approximately the same time.

In order to facilitate the fixing of staple on the anvil, the anvil may be disposed by a step below a slide, on which a row of staples is slidably displaceable, the height h of the step and the diameter d of the staple material having the relationship $0.25d \leq h \leq d$. The step will effectively support the staple which is to be deformed, also on the rear side of its crown, against tipping, and will guide it.

A first handle may be rigidly connected to a housing holding the magazine, the driver and further parts of the instrument. A two-armed lever, a longer arm of which provides a second handle, may be pivotable about an axis against and with spring action relative to the housing and the first handle, in order to displace the driver by means of a shorter arm of the lever. The driver and the hold-down device may be provided with aligned openings in which the shorter arm of the lever engages, the driver and the hold-down device being provided with laterally projecting tongues. A compression spring fixed between the tongues, holds the driver and the hold-down device in a given position with respect to each other, such position being determined by a stop.

When the handles are pressed together, the shorter arm of the lever acts on the tongue on the driver to displace the driver and the hold-down device towards the anvil, firstly together with each other up to said intermediate position, and then to move the driver alone relative to the hold-down device, which is then stationary. Such means for moving the driver and the hold-down device are simple and reliable.

BRIEF DESCRIPTION OF THE DRAWINGS

FIG. 5 is a rear elevation showing a hold-down device and a driver of the instrument in two different positions (shown side-by-side) relative to an anvil of the instrument;

FIGS. 6 and 7 are side views shown in longitudinal section of the hold-down device and of the driver in respective operating positions;

DETAILED DESCRIPTION OF THE INVENTION

Figure 1:
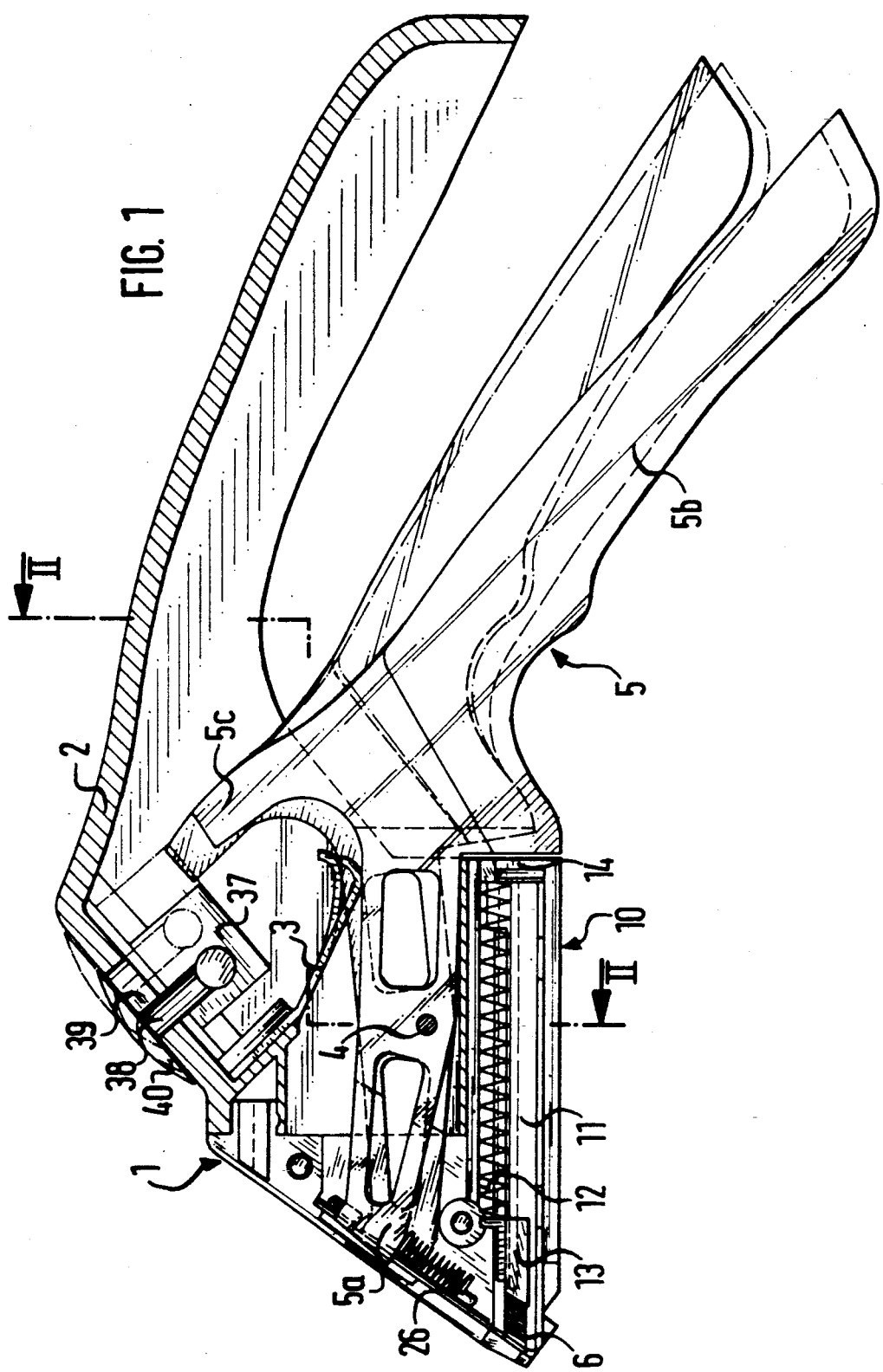
FIG. 1 is a side view, shown partly in section, of a surgical instrument according to an embodiment of the invention.
Figure 2:
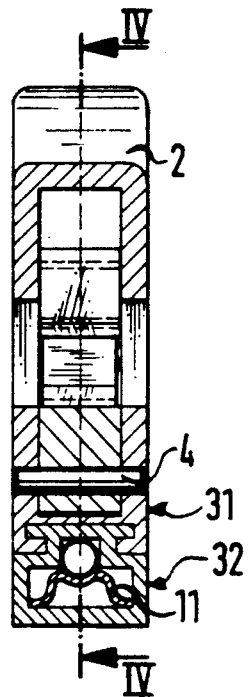
FIG. 2 is a sectional view taken on the lines II—II of FIG. 1.
Figure 3:
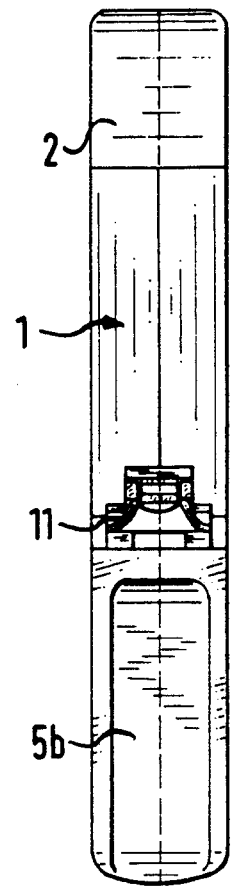
FIG. 3 is a front end view of the surgical instrument.
Figure 4:
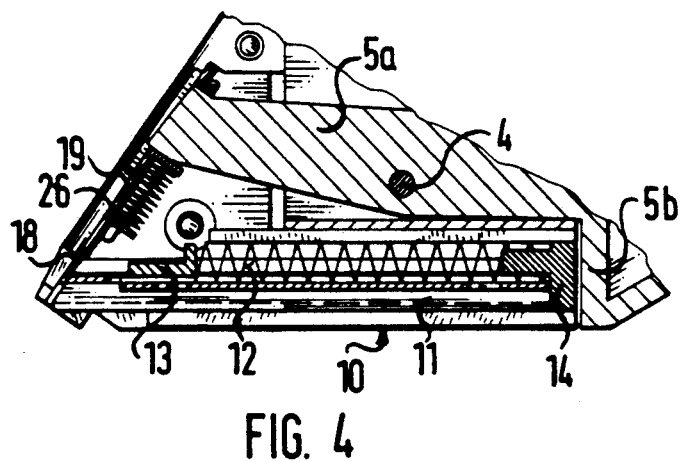
FIG. 4 is a sectional view taken on the lines IV—IV in FIG. 2.

An implantation surgical instrument for the application of surgical staples to wounds, comprises a housing 1 connected to a handle 2, relative to which a two-armed lever 5 is manually orientable about an axis 4, against the action of a spring 3 secured to the housing 1. The lever 5 comprises a shorter lever arm 5a, and a longer lever arm 5b which provides a second handle. Said handles are urged into relatively spaced relationship as shown in FIG. 1, by the action of the spring 3.

Figure 8:
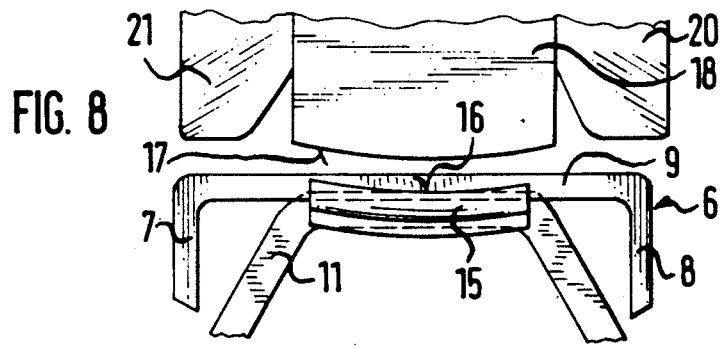
FIGS. 8 to 11 are diagrammatic, fragmentary elevational views illustrating, respective stages in the operation of staple deforming tooling of the instrument.

Surgical wound staples 6, each consisting of two legs 7 and 8 provided with teeth or points, and a crown 9 connecting the legs 7 and 8 (FIG. 8), are stored in a magazine 10 in succession in the form of a row of staples. The magazine 10 comprises a slide 11, on which the staples 6 are slidably displaceable towards a distally opening end of the housing 1, into the region of action of staple deforming tooling (described below), by means of a compression spring 12, one end presses against a shoe 13 slidable freely on the slide 11, the other end of which is fixedly supported by a part 14. As will be apparent from FIG. 1, the shoe 13 urges the row of staples towards said distally opening end.

As shown in FIG. 6 an anvil 15 formed on the slide 11 is located by a step below the adjacent end of the slide 11 so that the leading staple 6, is, before its deformation, positioned above the anvil 15 and is forced onto the anvil, only when the instrument is actuated.

The height h of said step and the diameter d of the staple material are expediently dimensioned to have the following relationship with respect to each other: $0.25d \leq h \leq d$, whereby sufficient rear support and guidance is afforded for the staple which is to be moved onto the anvil, and the distance that the staple has to be moved onto the anvil is not unnecessarily long.

Figure 9:
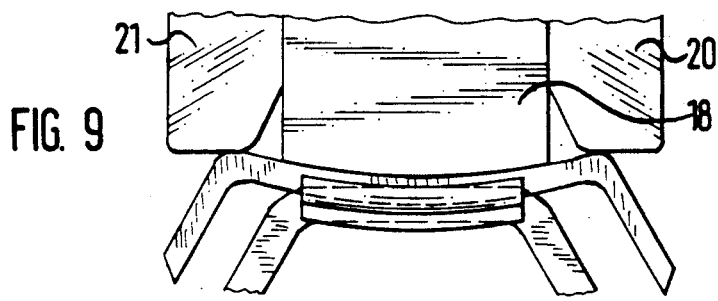

As best seen in FIGS. 5 and 8 to 11 the anvil 15 has a concave depression 16 extending transversely over its width, with which the convex end 17 of a hold-down device 18 is aligned, so that the staple 6 undergoes elastic deformation in the region of its crown 9 by the hold-down device 18, when it is lowered towards the anvil 15 and thus towards the staple (FIG. 9). Said deformation is directed in opposition to the actual direction of closing of the staple. The radii of the convex end 17 of the hold-down device and that of the depression 16 are substantially identical, and, depending on the shape of the stable and the staple material, are of the order of 60 to 80 mm, preferably of the order of 65 to 75 mm. The radius of the end 17 of the hold-down device may be 69 mm and the radius of the depression may be 70 mm. The radii within the above-mentioned orders of magnitude are generally selected so as to be the smaller, the greater is the strength or elastic limit of the staple material.

The hold-down device 18 and a driver 19 (FIGS. 5 to 6 and 12) cooperating therewith are produced from sheet metal stock by punching and stamping, there being provided on the driver 19, for the closure of the staple, in a known manner, two downwardly projecting legs 20 and 21, which pass the anvil 15 laterally (FIGS. 10 and 11) when the driver 19 is lowered.

The lower end 17 of the hold-down device 18 and the ends of the legs 20 and 21 which act in the deformation of the staple are chamfered (FIG. 7), so that the staple, on closure thereof to staple the wound, is securely held in the chamfers, so that it cannot tilt either forwardly or rearwardly.

The driver 19 and the hold-down device 18 have aligned openings or cut-outs 22 and 23, in which the free end of the lever arm 5a engages. The driver 19 and the hold-down device 18 are provided with rearwardly projecting tongues 24 and 25, respectively, between which is fixed a compression spring 26 which retains the driver 19 and the hold-down device 18 in a fixed position with respect to each other (FIG. 6). Said fixed position is determined by a hooked stop 27 formed on the driver 19, and which engages in the opening or cut-out 23 of the hold-down device 18 and rests against the upper inner edge of the opening or cut-out 23.

When the handles 2 and 5b are pressed together, the lever arm 5a exerts pressure on the tongue 24, so that the driver 19 and the hold-down device 18 are initially displaced together, from an upper position of rest, downwards into an intermediate position (FIG. 6), without being thereby displaced relative to each other. Initially, therefore, the end 17 of the hold-down device 18 strikes the crown 9 of the leading staple 6 emerging from the magazine 10, and pushes it downwards onto the anvil 15. As the handles 2 and 5b are further pressed together, the hold-down device 18 presses the crown 9, with as far as possible only elastic deformation thereof, into the depression 16 (FIG. 9) of the anvil 15. To this end the spring 26 should be so dimensioned that the driver 19 has not already been displaced downwards relative to the hold-down device, although such displacement can be permitted to a limited extent, in so far as it is still ensured that the legs 20 and 21 of the driver 19 have not already come to rest against the staple 6 and do not prevent the elastic spreading apart of the staple.

Figure 10:
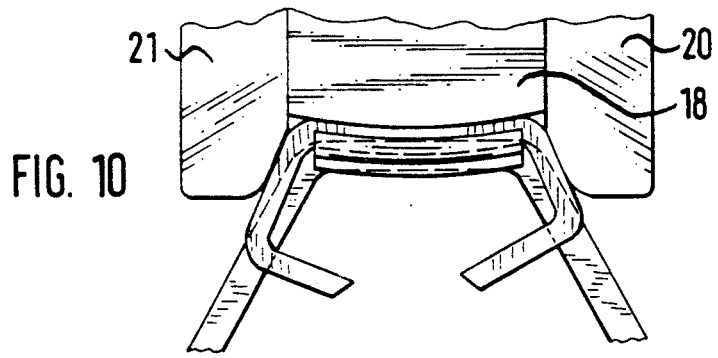
Figure 11:
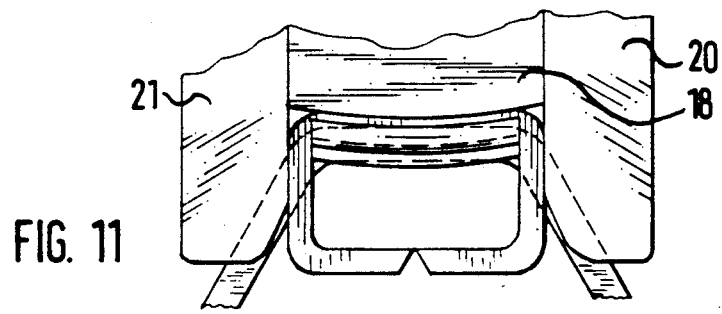

The hold-down device 18 cannot move further downwards after reaching the position of FIG. 9, so that the lever arm 5a, which is pressed down onto the tongue 24, will only move the driver 19, which is slidably guided on the hold-down device 18, further downwards, whereby the legs 20 and 21 of the driver 19 finally strike the staple legs 7 and 8 (FIG. 9) and deform them for closure of the staple by bending them about the lateral edges of the anvil 15 (FIGS. 10 and 11). The spring 26 is continuously more strongly compressed. The greatest possible travel of the spring 26 in this respect, and also the greatest possible downward displacement of the driver 19 relative to the hold-down device 18 can be predetermined by providing an edge 28 on the driver 19, and a step 29 on the hold-down device 18, the edge 28 and the step 29 abutting each other in the end position shown in FIG. 7. Additionally, or alternatively, said downward displacement can be limited by means of a spacer pin 30 provided between the driver 19 and the hold-down device 18, the pin 30 may project vertically from the tongue 25 (FIG. 6), the free end of the pin 30 butting against the tongue 24 from below as a stop, as soon as the end position of FIG. 7 is reached.

When the hand closing the handles 2 and 5b has been opened, the spring 3 returns the lever 5 to its initial position (FIG. 1) and at the same time the lever arm 5b, which is moved in a clockwise (as seen in FIG. 1) sense with the cooperation of the slackening spring 26, moves the hold-down device 18 and the driver 19 upwards into their positions of rest, so that the implanted staple 6 can be released from the instrument simply by shedding off from the anvil 15.

As soon as the driver 19 moves upwards, out of contact with the staple, the staple tends partially to open, that is to say spread apart, again, since it was elastically deformed in the closing direction by means of the driver 19. Such spreading apart of the staple is counteracted, however, by the elastic deformation of the staple brought about by the hold-down device 18, so that such disadvantageous spreading apart of the staple is at least largely compensated for.

Figure 12:
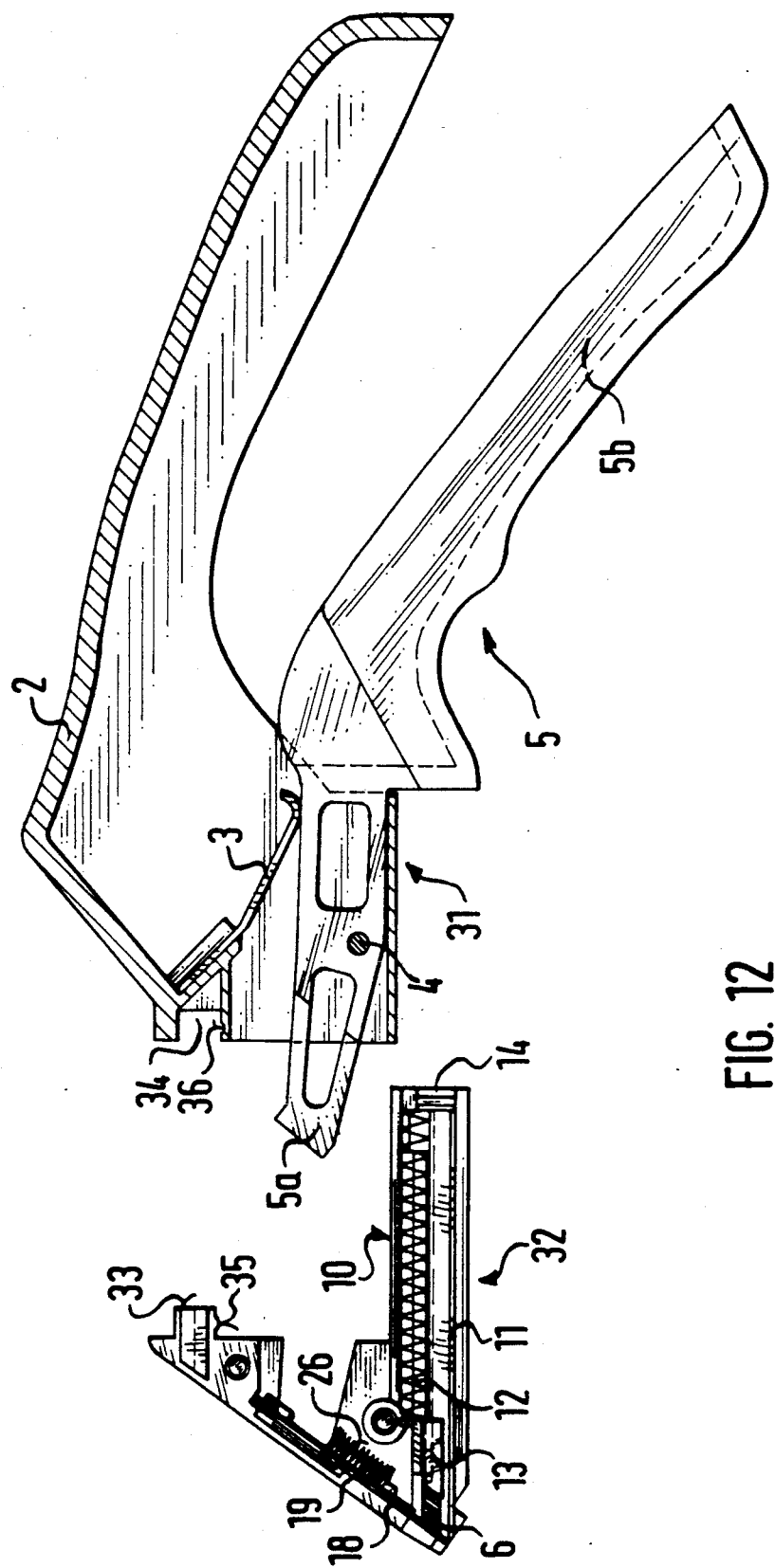
FIG. 12 is a similar view to that of FIG. 1 but showing a modified form of the surgical instrument.

The magazine 10, with staples and also other parts, such as, for example, the hold-down device 18, the driver 19 and a part of the housing, may be constructed as a separate structural unit, which, can, as a disposable item, be detachably secured by insertion, to the remainder of the housing. The other parts of the instrument are such as to be sterilisable, for multiple use, for reasons of economy. As shown in FIG. 12, a first part 31 of the instrument is for reuse and a second part 32 of the instrument is interchangeable for once-only use. As shown in FIG. 12, both of the parts 31 and 32 have guides which lockably engage each other in the region above the slide 11, so that the parts 31 and 32 can be engaged with, and detached from, each other. The part 32 has an upper extension 33 which when the parts 31 and 32 are being joined together, engages in a holding fixture 34 of the part 31, thereby to provide a detent connection, a nose 35 on the extension 33 snapping into a recess 36 in the holding fixture 34. The instrument housing must accordingly be constructed in two parts, and the end of the short lever arm 5a must engage freely through the openings 22 and 23 of the driver 19 and of the hold-down device 18 and must not be fixedly connected therewith.

The interchangeable part 32 comprises, in particular, the magazine 10 with the slide 11 and the anvil 15, the compression spring 12, the shoe 13 and the staples 6, and also the driver 19 and the hold-down device 18 with the spring 26 acting therebetween, and finally the front part of the instrument housing 1. Essential components of the reusable part 31 are the double-armed lever 5, the handle 2, the axis 4, the spring 3 and the rear part of the instrument housing 1.

It is of particular importance that, inter alia, the dies, as components for deforming the staple, are included in the interchangeable part 32. In instruments as disclosed in DE-B-31 34 63 and DE-A-36 15 405, in which mainly only the magazine and possibly also the anvil are interchangeable, the driver is included in the reusable part of the instrument, and therefore always remains directly connected to the lever, for moving the driver. This has the disadvantage that the dies, after replacement of the disposable part may not fit together exactly, especially since the driver will wear over a period of time, leading to deficient deformation of the staple. Both of the dies must, therefore be exchanged together with the magazine.

For connecting a wound edge in the region of large tissue swellings, and also in order to avoid excessive injury to the lower skin, for example in fixing skin transplants, the application of the staples should be adapted to a wound having a variable edge, the staple being incompletely deformed, as shown in FIG. 11, but rather only partially closed, as shown for example in FIG. 10.

To this end the extent of staple deformation may be made variable by means of an adjustable stop delimiting the maximum possible movement of one of the handles. FIG. 1 shows a stop 37 connected, by way of a crosspiece 38 which engages in an elongate hole 39 in the rear housing part, to a slide 40 which is externally accessible. An extension 5c on the lever 5, can, in the position of the stop 37 and the slide 40, shown in full lines, freely pass the stop 37 upon closure of the handles 2 and 5b, so that the staple is completely deformed.

If, however, the slide 40 and thus the stop 37 are moved obliquely upwards into the position shown in broken lines, the free end of the extension 5c will strike the stop 37 as the handles 2 and 5b are closed, thereby preventing further pivotal movement of the lever 5 and further downward movement of the driver 19 so that the staple can not be completely deformed.

What is claimed is:

1. A surgical instrument for implanting in bodily tissue, wound staples each comprising two legs connected by a crown, said instrument comprising:
    an anvil;
    a magazine for the staples, associated with the anvil and having means for moving staples successively out of the magazine and on to the anvil;
    a driver for deforming a staple on the anvil;
    means for lowering the driver from a rest position towards the anvil to deform said staple thereon to bend it about the anvil thereby to close said staple, and to insert the legs thereof into said bodily tissue;
    a hold-down device; and
    means for lowering the hold-down device onto the anvil, to press the crown of said staple thereon towards the anvil concomitantly with the deformation of said staple by said driver.

2. An instrument as claimed in claim 1, wherein the anvil has a concave depression, the hold-down device having a convex end aligned with said depression, whereby when said convex end is pressed against the crown of said staple on the anvil, said staple undergoes elastic deformation in the region of the crown thereof in opposition to the direction of closing of the staple.

3. An instrument as claimed in claim 2, wherein the radius of said convex end is substantially equal to that of said depression, being of the order of 60, to 80 mm.

4. An instrument as claimed in claim 3, wherein the radii of said convex end and of said depression are of the order of 65 mm to 75 mm.

5. An instrument as claimed in claim 1, wherein the driver is movable with the hold-down device from said rest position to an intermediate position in which the hold-down device rests upon the crown of said staple on the anvil, a spring mechanism acting between the driver and the hold-down device, the driver alone being movable further downward from the intermediate position in order to deform the staple while the hold-down device rests in the intermediate position and the spring mechanism is compressed.

6. An instrument as claimed in claim 1, comprising a housing holding the magazine; a first handle rigidly connected to the housing and the driver; and a two-armed lever having a shorter arm, and a longer arm providing a second handle, and being pivotable with respect to the housing and to the first handle, about an axis, against the action of resilient means, to cause said shorter arm to move the driver, the hold-down device and the driver being provided with aligned openings engaged in by said shorter arm, and with laterally projecting tongues, a compression spring fixed between said tongues being provided for holding the driver and the hold-down device in a given position with respect to each other, a stop being provided for determining such position; whereby upon said first and second handles being pressed towards each other said shorter arm of the lever acts upon the tongue on the driver to move the driver and the hold-down device towards the anvil, firstly together with each other up to an intermediate position in which the hold-down device acts upon the crown of said staple on the anvil, and then to move the driver alone relative to the hold-down device in order to deform said staple on the anvil, the hold-down device being stationary.

7. An instrument as claimed in claim 6, comprising a stop which is adjustable to limit the displacement of said second handle thereby to delimit the extent of deformation of said staple on the anvil.

8. An instrument as claimed in claim 1, comprising stops for delimiting the greatest downward movement of the driver relative to the hold-down device.

9. An instrument as claimed in claim 1, wherein the magazine comprises a slide along which a row of said staples is slidably displaceable, the anvil being spaced from the slide therebelow by a step, the height h of said step and the diameter of the d of the staple material having the relationship $0.25d \leq h \leq d$.

10. An instrument as claimed in claim 1, comprising a reusable first instrument part and a second instrument part detachably connected to said first instrument part and comprising the magazine which is interchangeable, the anvil, the driver and the hold-down device also being associated with the second instrument part.

11. An instrument as claimed in claim 10, comprising a detent connection for holding said instrument parts together.

12. An instrument as claimed in claim 1, comprising a stop which is adjustable to delimit the extent of deformation of said staple on the anvil.

* * * * *